US007435226B2

(12) United States Patent
Suarez

(10) Patent No.: US 7,435,226 B2
(45) Date of Patent: Oct. 14, 2008

(54) METHOD AND APPARATUS FOR DISPLAYING INFORMATION OBTAINED BY ELECTRICAL IMPEDANCE TOMOGRAPHY DATA

(75) Inventor: Fernando Sipmann Suarez, Madrid (ES)

(73) Assignees: Stephan Bohm, Hamburg-Eppendorf (DE); Marcelo B. P. Amato, Sao Paulo (BR)

( * ) Notice: Subject to any disclaimer, the term of this patent is extended or adjusted under 35 U.S.C. 154(b) by 1133 days.

(21) Appl. No.: 10/310,988

(22) Filed: Dec. 6, 2002

(65) Prior Publication Data

US 2003/0216664 A1 Nov. 20, 2003

Related U.S. Application Data

(63) Continuation of application No. PCT/EP01/06523, filed on Jun. 8, 2001.

(30) Foreign Application Priority Data

Jun. 9, 2000 (EP) .................................. 00111879

(51) Int. Cl.
*A61B 5/08* (2006.01)
*A61B 5/05* (2006.01)
(52) U.S. Cl. ........................ 600/536; 600/529; 600/547
(58) Field of Classification Search ................. 600/300, 600/301, 547, 529–543, 481, 484, 509, 513, 600/522
See application file for complete search history.

(56) References Cited

U.S. PATENT DOCUMENTS 5,311,878 A * 5/1994 Brown et al. ................. 600/547
5,465,730 A * 11/1995 Zadehkoochak et al. .... 600/547

| | | | |
|---|---|---|---|
| 5,626,146 A * | 5/1997 | Barber et al. | 600/547 |
| 5,810,742 A | 9/1998 | Pearlman | |
| 6,055,452 A * | 4/2000 | Pearlman | 600/547 |
| 6,236,886 B1 * | 5/2001 | Cherepenin et al. | 600/547 |
| 6,308,097 B1 * | 10/2001 | Pearlman | 600/547 |
| 6,421,559 B1 * | 7/2002 | Pearlman | 600/547 |

(Continued)

FOREIGN PATENT DOCUMENTS

EP 1000580 5/2000

OTHER PUBLICATIONS

B.H. Brown et al, Simultaneous Display of Lung Ventilation and Perfusion on a Real-Time EIT System, IEEE, Publication Date: Oct. 29, 1992, p. 1710.

(Continued)

*Primary Examiner*—Charles A. Marmor, II
*Assistant Examiner*—Navin Natnithithadha
(74) *Attorney, Agent, or Firm*—Shlesinger, Arkwright & Garvey LLP

(57) ABSTRACT

The invention refers to a method and an apparatus for displaying information obtained by electrical impedance tomography (EIT) data from a part of a patient's body. In order to provide a method for displaying information which can be immediately used in order to determine a specific pathological condition of said part, a method according to the invention performs te following steps: processing the EIT data with a plurality of predetermined processing modes; determining specific pathological conditions of said part in accordance with the results of the predetermined processing modes; selecting a screen mode from a plurality of predetermined screen modes in accordance with the specific pathological conditions; and displaying the EIT data in accordance with the selected screen modes.

44 Claims, 12 Drawing Sheets

U.S. PATENT DOCUMENTS 6,501,984 B1 * 12/2002 Church et al. ............... 600/547
6,678,552 B2 * 1/2004 Pearlman .................... 600/547
7,096,061 B2 * 8/2006 Arad .......................... 600/547
7,141,019 B2 * 11/2006 Pearlman .................... 600/437

OTHER PUBLICATIONS

A.M. Dijkstra et al., "Review: Clinical applications of electrical impedance tomography", Journal of Medical Engineering & Technology, vol. 17, No. 3 (May/Jun. 1993), pp. 89-98.

* cited by examiner

FIG. 1
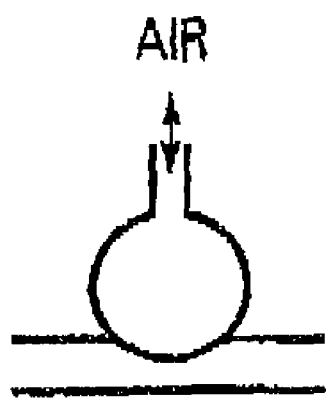
**A-
VENTILATED
AND PERFUSED**
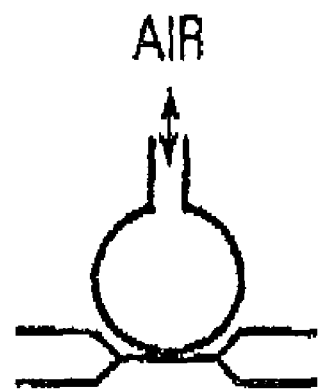
**B-
VENTILATED
AND NOT PERFUSED**
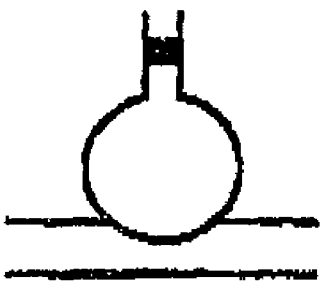
**C-
PERFUSED AND
NOT VENTILATED**
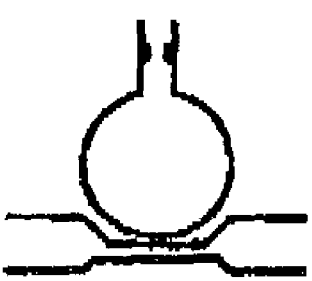
**D-
POORLY PERFUSED
POORLY VENTILATED**

FIG.4a

| PROCESSING MODE / SPECIFIC LUNG CONDITION | RELATIVE MODE | PERFUSION MODE | ABSOLUTE MODE |
|---|---|---|---|
| PULMONARY INFARCT | ↓ | ↓ | ↑ |
| PULMONARY EMBOLISM | NORMAL | ↓ | NORMAL |
| LOCALIZED PNEUMONIA | ↓ | ↑ | ↓ |
| EMPHYSEMA- LIKE AREA | ↓ | ↓ | ↑ |

FIG.4b

| SCREEN MODE / SPECIFIC LUNG CONDITION | FUNCTIONAL IMAGE ACC. RELATIVE MODE IN SPECIFIC AREA | FUNCTIONAL IMAGE ACC. PERFUSION MODE IN SPECIFIC AREA | FUNCTIONAL IMAGE ACC. ABSOLUTE MODE IN SPECIFIC AREA |
|---|---|---|---|
| PULMONARY INFARCT | ↓ | ↓ | ↑ |
| PULMONARY EMBOLISM. | NORMAL | ↓ | NORMAL |
| LOCALIZED PNEUMONIA | ↓ | ↑ | ↓ |
| EMPHYSEMA- LIKE AREA | ↓ | ↓ | ↑ |

FIG. 5a

| SPECIFIC LUNG CONDITION \ PROCESSING MODE | RELATIVE MODE | PERFUSION MODE | ABSOLUTE MODE | RELATIVE/ PERFUSION MODE (V/Q) |
|---|---|---|---|---|
| PULMONARY INFARCT | ↓ | ↓ | ↓ | ↓ |
| PULMONARY EMBOLISM | NORMAL | ↓ | NORMAL | ↑↑↑ |
| LOCALIZED PNEUMONIA | ↓ | ↑ | ↑ | ↓↓↓ |
| EMPHYSEMA-LIKE AREA | ↓ | ↓ | ↓ | ↓↑ |

FIG. 5b

| SPECIFIC LUNG CONDITION \ SCREEN MODE | FUNCTIONAL IMAGE ACC. RELATIVE MODE IN SPECIFIC AREA | FUNCTIONAL IMAGE ACC. PERFUSION MODE IN SPECIFIC AREA | FUNCTIONAL IMAGE ACC. ABSOLUTE MODE IN SPECIFIC AREA | FUNCTIONAL IMAGE ACC. V/Q MODE IN SPECIFIC AREA |
|---|---|---|---|---|
| PULMONARY INFARCT | ↓ | ↓ | ↓ | ↓ |
| PULMONARY EMBOLISM | NORMAL | ↓ | NORMAL | ↑↑↑ |
| LOCALIZED PNEUMONIA | ↓ | ↑ | ↑ | ↓↓↓ |
| EMPHYSEMA-LIKE AREA | ↓ | ↓ | ↓ | ↓↑ |

FIG.6a

| PROCESSING MODE / SPECIFIC LUNG CONDITION | RELATIVE MODE | PERFUSION MODE | ABSOLUTE MODE |
|---|---|---|---|
| PNEUMOTHORAX | 0 | 0 | ← |
| PLEURAL EFFUSSION | 0 | 0 | → |
| ATELECTASIS | → | → | ← |
| OVERDISTENSION | → | → | ← |

FIG.6b

| SCREEN MODE / SPECIFIC LUNG CONDITION | FUNCTIONAL IMAGE ACC. RELATIVE MODE IN SPECIFIC AREA | FUNCTIONAL IMAGE ACC. PERFUSION MODE IN SPECIFIC AREA | FUNCTIONAL IMAGE ACC. ABSOLUTE MODE IN SPECIFIC AREA |
|---|---|---|---|
| PNEUMOTHORAX | 0 | 0 | ← |
| PLEURAL EFFUSSION | 0 | 0 | → |
| ATELECTASIS | → | → | ← |
| OVERDISTENSION | → | → | ← |

*FIG. 7a*

| PROCESSING MODE / SPECIFIC LUNG CONDITION | RELATIVE MODE | PERFUSION MODE | ABSOLUTE MODE | RELATIVE/ PERFUSION MODE (V/Q) |
|---|---|---|---|---|
| PNEUMOTHORAX | 0 | 0 | ← | NOT AVAILABLE |
| PLEURAL EFFUSSION | 0 | 0 | → | NOT AVAILABLE |
| ATELECTASIS | → | → | → | ↓↓ |
| OVERDISTENSION | → | → | ← | ↓↓ |

*FIG. 7b*

| SCREEN MODE / SPECIFIC LUNG CONDITION | FUNCTIONAL IMAGE ACC. RELATIVE MODE IN SPECIFIC AREA | FUNCTIONAL IMAGE ACC. PERFUSION MODE IN SPECIFIC AREA | FUNCTIONAL IMAGE ACC. ABSOLUTE MODE IN SPECIFIC AREA |
|---|---|---|---|
| PNEUMOTHORAX | 0 | 0 | ← |
| PLEURAL EFFUSSION | 0 | 0 | → |
| ATELECTASIS | → | → | → |
| OVERDISTENSION | → | → | ← |

FIG.8a

| SPECIFIC LUNG CONDITION \ PROCESSING MODE | RELATIVE MODE | PHASE-LAG MODE | ABSOLUTE MODE |
|---|---|---|---|
| PATENT AIRWAY | NORMAL | NORMAL | NORMAL |
| CYCLIC AIRWAY CLOSURE | ↑ | ↑↑ | ↑↓ |
| PERSISTENT AIRWAY CLOSURE WITH AIR-TRAPPING | ↓↓ | ↑↑ (180°) | ↑↓ |
| PERSISTENT AIRWAY CLOSURE WITH RE-ABSORPTION ATELECTASIS | ↓↓ | ↑↓ | ↓↓ |

FIG.8b

| SPECIFIC LUNG CONDITION \ SCREEN MODE | FUNCTIONAL IMAGE ACC. RELATIVE MODE | FUNCTIONAL IMAGE ACC. PHASE-LAG MODE |
|---|---|---|
| PATENT AIRWAY | NORMAL | NORMAL |
| CYCLIC AIRWAY CLOSURE | ↑ | ↑↑ |
| PERSISTENT AIRWAY CLOSURE WITH AIR-TRAPPING | ↓↓ | ↑↑ (180°) |
| PERSISTENT AIRWAY CLOSURE WITH RE-ABSORPTION ATELECTASIS | ↓↓ | ↑↓ |

METHOD AND APPARATUS FOR DISPLAYING INFORMATION OBTAINED BY ELECTRICAL IMPEDANCE TOMOGRAPHY DATA

This is a continuation application of PCT/EP01/06523, filed Jun. 8, 2001, claiming the priority benefit of European Application No. 00111879.3, filed Jun. 9, 2000.

FIELD OF THE INVENTION

The invention refers to a method and an apparatus for displaying information obtained by electrical impedance tomography (EIT) data from a part of a patient's body.

BACKGROUND OF THE INVENTION

The electrical impedance tomography takes advantage of the differing specific conductivity of human tissues, which varies from 15.4 mS/cm for cerebrospinal fluid to 0.06 mS/cm for bone. The difference in the value of conductivity is large between different tissues. Cross sectional images of the distribution of conductivity or alternatively specific resistance therefore show a good contrast. The aim of electrical impedance tomography is to produce images of those contrasts.

An example of carrying out an EIT measurement is the analysis of a patient's lang. A number of electrodes are placed around the thorax, wherein an alternating current with e.g. 50 kHz at 5 nA peak to peak amplitude is applied to respectively adjacent electrodes. The other electrodes respectively are used with the alternating current to carry out the measurement of impedance against a defined reference potential. As soon as all the electrodes, one after another, have served as current conducting electrodes, a cycle for data detection is concluded in order to eliminate statistical disturbances, as a rule a plurality of data detection cycles is averaged, in order to obtain a corresponding picture.

The maximum impedance changes in the zone of the thorax are caused by breathing in and out of air. In this context it can be observed that the impedance change which is measured by electrodes is a measure of the change of volume in the lung. Therefore, according to the process of EIT, measurements can also be carried out with respect to the pressure-volume relationship of the lung.

The complete reconstruction problem is non-linear and requires iteration. However, each step in the iterative process is linear. Images reconstructed using only the first step of iteration effectively treat image formation as a linear process, an assumption approximately justified for small changes in conductivity from uniform. Most of the clinical images produced today are using a single-step reconstruction algorithm.

One aim of EIT is to reconstruct images of the absolute distribution of conductivity. These images are known as absolute images. However, this requires that the forward problem can be solved to a high degree of accuracy, and this can be difficult. The magnitude of the voltage signal measured on an electrode or between electrodes will depend on the body shape, the electrode shape and position, and the internal conductivity distribution. The signal magnitude is in fact dominated by the first two effects rather than by conductivity. However, it a change in conductivity occurs within the object, than it can often be assumed that the change in surface voltage is dominated by this conductivity change. In differential imaging, the aim is to image changes in conductivity rather than absolute values.

Differential algorithms can only image changes in conductivity. Absolute distributions of conductivity cannot be produced using these methods. In addition, any cross movement of the electrodes, either because they have to be removed and replaced or even because of significant patient movement, make the use of this technique difficult for long-term measurement of changes. As an alternative to changes in time, differential algorithms can images changes in conductivity with frequency, Measurements can be made over a range of frequencies and differential images can be produced using data from the lowest frequency and the other frequencies in term. A multi-frequency measurement thereby makes use of the complex resistance of a tissue which depends on the frequency.

As it becomes obvious, the analysis of a patient's lung by electrical impedance tomography yields a vast amount of data. An BIT image consists of a plurality of pixels, wherein each pixel can be determined by different reconstruction techniques as described above, i.e. by the determination of the absolute distribution, the relative distribution or distribution over a range of frequencies.

On the other hand, there are also a plurality of lung conditions which have to be determined from the plurality of EIT data. Basically, this derives from the fact that in the lung there are theoretically four types of alveoli, which is shown in FIG. 1. The normal alveolus (A) is both ventilated and perfused with blood, There are alveoli that are ventilated, but not perfused (B); such alveoli contribute significantly to the physiologic dead space. There are alveoli that are not ventilated, but perfused (C); such alveoli do not provide the exchange of respiratory gases. Finally, there are alveoli that are both poorly ventilated and poorly perfused (D); such alveoli contain high $CO_2$ and $N_2$ and $O_2$. These alveoli are the last to expel their $CO_2$ and $N_2$ in washout tests.

An experienced doctor is able to use the plurality of EIT data in order to determine the plurality of different lung conditions. This is conventionally done by analysing the different types of reconstruction images according to the absolute distribution, the relative distribution and the distribution over a certain range of frequency. However, even for an experienced doctor it is still very time-consuming using a conventional EIT monitor to come to sufficient results.

OBJECTS AND SUMMARY OF THE INVENTION

Therefore, it is an object of the invention to provide a method for displaying information obtained by electrical impedance tomography data from a part of a patient's body which can be immediately used in order to determine the respective pathological condition of said part.

This object is solved by a method and an apparatus as described herein. The inventive method comprises the steps of:
  processing the SIT data with a plurality of predetermined processing modes;
  determining specific pathological conditions in accordance with the results of the predetermined processing modes;
  selecting at least one screen mode from a plurality of predetermined screen modes in accordance with the specific lung conditions; and
  displaying the EIT data in accordance with the selected screen modes.

In the following, six predetermined processing modes according to the invention are explained in the case of analysing a patient's lung. These modes are
  the relative mode,
  the phase-lag mode, the perfusion mode,
the absolute mode,
the time constant mode and
the regional spirometry mode.

Relative Mode

The relative mode calculates regional changes of a bi-dimensional distribution of tidal ventilation during a time period in the past. The regional changes in impedance are obtained off-line by electric impedance tomography at discrete time intervals utilizing a technique capable of estimating relative variations in impedance (percent variations, for instance). Relative variations in impedance are calculated by using a simplified model of the region, mathematically representing the cross sectional plane of the thorax containing the electrodes, The simplified model is obtained through a variety of methods, like the finite element method, or finite differences, or even Eigen-function superposition. Computation of relative changes in impedance implies the choice of a reference. This reference may be a set of boundary voltages or a vector of impedance distributions in the region of interest, obtained in a past moment or during a time interval in the past. This particular moment or interval of reference is chosen manually or automatically. After the completion of a certain time period, a sequence of relative impedance changes for each pixel is available, and some measurement of its variance along the time is calculated. The variance estimation is a statistical measure of dispersion, like amplitude, standard deviation, or others.

Phase-Lag Mode

The phase-lag mode processes the dynamics of tidal ventilation and is an index of the homogeneity of the lung dynamics. Values can be displayed for inspiration, expiration or for the whole respiratory cycle. Narrow ranges represent the typical homogeneous behaviour of lungs with healthy airways and alveoli. Larger ranges are indicative of severe airway and alveolar disease.

FIG. 2 shows the processing of EIT data according to the phase-lag mode.

During monotonous tidal ventilation, the phase angle of each pixel is calculated when compared to the sinusoidal or some other approximating function of the overall impedance oscillation during tidal breaths. By considering all pixels representing a lung area, the overall impedance oscillation represents the average impedance oscillation. The individual pixel oscillations will be compared to this overall oscillation for phase lag detection. The overall impedance oscillation, as well as the individual pixel oscillation, is calculated by relative electric impedance tomography at discrete time intervals, as described above. A negative phase angle means that a certain pixel is being inflated/deflated earlier than the average lung oscillation, whereas a positive phase angle means that the pixel represents a lung zone with a delayed inflation/deflation pattern. Each pixel has a phase angle representing it.

Perfusion Mode

The perfusion mode processes the bi-dimensional distribution of lung perfusion during a time period in the past. The same principles used for the relative mode (described above) are applied here. The only particular aspects are as follows: The sampling rate has to be>20 Hertz. Cardiac related changes in resistivity in the lungs are smaller (about 5-10% of those related to breathing movements) and occur at an oscillatory frequency ten times higher. The whole cycle of lung perfusion oscillation has precisely the length of the electrical cardiac cycle (usually in the range of 0.5 to 1 sec). After the completion of a certain window of time, a sequence of cardiac-related-relative-impedance-changes is available and some measurement of its variance along the time is calculated off-line. The variance estimation can be any statistical measure of dispersion like standard deviation, variance per se or others. The pixel values will be proportional to this estimate of dispersion (for each pixel) during the time period in question.

To improve the quality of the perfusion signals of EIT an apnea period is introduced. During apnea, we assume that the dispersion measure is proportional to the regional perfusion. Alternatively, the patient can be ventilated at a respiratory rate well below (less than ⅓) the cardiac rate, and a high-pass filter can be used to remove breath related changes in impedance.

Considering a fixed cardiac output, the amplitudes of impedance oscillations along the cardiac cycle are proportional to the relative blood perfusion into a certain lung region. Considering two equally sized lung regions or pixels, the one showing the highest oscillation related to cardiac cycles is the one receiving a greater proportion of the cardiac output.

In order to increase the amount of information obtained from a lung perfusion EIT image even further, it is advisable to subdivide the entire cardiac cycle into its components As an example, consider a patient with a cardiac rate of 60 beats/min and a sampling rate of 50 Hertz. The hypothetical collection of subsequent sets of impedance distributions, at equally timed intervals, starting from the peak of QRS (the ventricular related electrical depolarisation detected on the ECG) and finishing 20 msec before the next QRS complex will reveal 3 waves of impedance changes:

First, a small fall in impedance is related to the contraction of the left atrium pushing blood back into the lungs. A second big fall in impedance is related to the stroke volume delivered to the pulmonary arteries by the right ventricle; and finally a third intermediate fall is due to the elastic recovery of the energy stored in pulmonary arteries, pushing blood through the pulmonary capillaries and veins. The whole cycle will be repeated, starting from the next QRS complex. An analysis of each of these sub-phases of the cardiac cycle can be performed separately using the same display functions as described previously for the other modes.

Absolute Mode

The absolute mode processes the estimated absolute impedance of each pixel, after correction for noise and electrode/skin impedance problems. Different from the algorithms for calculating relative changes in impedance, iterative mathematical algorithms are applied for stepwise convergence to the right solution (defined, for instance, as the impedance distribution in a ROX, generating the lowest possible squared error between the predicted boundary voltages and those actually measured). The convergence may be guided by some noise analysis. The pixel values represent an estimate of absolute impedance for each pixel–the average value during the data collection time.

As described above, the absolute mode processes the estimated absolute impedance of each pixel. Relative changes in impedance are computed directly by using one step methods; absolute impedance measurements, however, are obtained by iterative mathematical algorithms. The best estimated distribution is always an impedance distribution on the ROI that minimizes a certain error index. The error index may be defined in different ways, according to the observed differences between the predicted boundary voltages and those actually measured. The algorithm convergence may be guided by some noise analysis, as in the Kalman filter algorithm, several procedures may be used to filter noise as singular value truncation or coherent means of measured voltages.

To achieve the best quality of data, the patient has to be on static conditions during the data acquisition time, or the data acquisition interval shall be short relatively to the respiratory cycle. Alternatively, a long time period of data acquisition ban be used and some low-pass filtering process can be used.

In order to enhance the quality of the information obtained, we suggest to use more than one algorithm for the estimation of impedance distribution together, having two or more calculating procedures working in parallel. A slower but more precise algorithm can be used as a check procedure for the faster one. Genetic algorithms, neural nets, Newton Raphson methods or Kalman-Filter-based-algorithms can be used. Ambiguities in the solution of a fast algorithm can be solved by genetic algorithms, which progressively improve their performance along the time. Neural nets, previously trained with data collected from conventional CT or bedside clinical data, can improve the definition of common structures inside the thorax.

Once a sequence in time of absolute impedance distributions is computed, the relative impedance distribution can be obtained by algebraically subtracting two subsequent absolute distributions. Relative impedance changes computed by the non-linear models mentioned above are a better estimate of the true changes than the ones calculated by traditional back projection techniques.

In the absolute mode, aerated zones will be assigned with a high pixel value, whereas liquid/solid zones will be assigned with a low impedance value, independent of its variation along tidal breathing. Bubbles of trapped air (pneumothorax or bubbles of emphysema, for instance) will be represented by high impedance values, despite the fact that they would be assigned low values for variance/dispersion in the relative mode.

Because absolute impedance can be defined as an absolute number, with a dimension like Volts/Amperes/Pixel-Volume, the colours, tonalities, or elevations can have an absolute scale. Therefore, the overall colour of the lung inside the region of interest will provide immediate information about the degree of lung aeration/edema. Appropriate corrections for the thoracic circumference and subcutaneous fat and muscle can be provided with the help of an extensiometer or plethysmograph.

Time Constant Mode

FIG. 3 shows the processing of EIT data according to the time constant mode. During controlled mechanical ventilation or during special manoeuvres in the awake and spontaneously breathing patient (say a forced vital capacity manoeuvre) a special exponential approximation function is used.

The exponential fit process will be applied for the overall change of impedance (the whole region of interest), as well as the regional (per pixel) impedance changes. By using an exponential approximation during a relaxed expiration, the overall time constant and the time constants for each pixel can be estimated: i.e. the time period until a change corresponding to 63.2% of the total impedance change during a long exhalation (enough to achieve a stable plateau of impedance). The start of the running window can be synchronized with the beginning of exhalation by making use of a manual or automatic trigger.

In this particular case, pixel values will represent time constants displayed as colours or tonalities in a bi-dimensional graphic display (or by elevation on the z-axis, in a three-dimensional display). Because a time constant can be defined as an absolute number—with its dimension of seconds—the colours, tonalities, or elevations can have an absolute scale. Therefore, the overall colour of the lung inside the region of interest will provide immediate information about the degree of lung obstruction. Zone separations and ratio calculations can be performed.

Additionally, the dispersion of time constants can also be used as an index of airway disease. Any of the abovementioned statistical measure of dispersion can be used for this purpose.

Finally, the presence of units not achieving a stable plateau of impedance, even after a long expiration, constitutes also a signal of severe airway disease.

Regional Spirometry Mode

Spirometry is still one of the most important pulmonary function tests. It is used to determine specifically defined and standardized volumes—like the tidal volume of inhaled or exhaled breathing gases. By adding one or more of these volumes lung capacities—like the vital capacity (VC)—are determined. To date, a regional analysis of these volumes and capacities has not been possible without invasive or radioactive means.

An EIT monitor can enhance traditional spirometry by adding information about the regional distribution of the gross volumes within the lungs. In analogy with traditional spirometry, total but also regional volumes and capacities can be obtained by EIT. Time dependent volumes, like the $FEV_1$ (forced expiratory volume within the first second of exhalation) ban be determined on a regional as well as on a global basis. When observing volume changes versus time, a flow can be calculated and analysed for the entire lung, but also for a smaller region of interest within the lung. This way, pathologies with respect to compliance and resistance are detected not only on a global, but also on a regional lung level and the regional predominance of such a pathology can be identified.

Each pathological condition or each lung condition respectively can be determined for the whole lung or for a region of interest of the lung. In the latter case lung conditions with local spreading can be determined more precisely. For example, the patients lung can be divided up into four regions of interest, wherein for each region of interest a full determination of each lung condition by running all respective processing modes is performed. As a result, for each of the region of interest the respective lung conditions are determined wherein the determined lung conditions can differ between the several regions of interest.

According to one aspect of the invention, the determination of specific lung conditions in accordance with the results of the predetermined processing modes can be based on a knowledge based data bank which contains certain decision rules for each specific lung condition. The decision rules can be based, e.g. on Fuzzy Logic.

As to the different types of screen modes, according to the invention the following types of screen modes can be distinguished in the case of analysing a patient's lung:
  functional images,
  graphs,
  numerical values and
  others.

Functional Images

A functional image is an online imaging of the patient's lung on the basis of an actual processing mode. Thus, functional images form a screen mode which are a graphic representation of the underlying data for the automatic determination of the specific lung conditions. Each pixel is displayed according to its distribution and is preferably averaged over time by applying a running window of e.g. 5-30 seconds. The location of each pixel in the functional image presents the estimate of its spatial location inside the thorax, considering the plane embracing all electrodes. Alternatively, a pixel value can be represented by its evaluation on a third axis, using a three-dimensional display.

Taking for example the relative or differential distribution of conductivity, during the running window of time the regional changes of electric impedance in each pixel within the two-dimensional plane embracing all the electrodes are allocated. After the completion of a certain window of time, a sequence of relative impedance changes for each pixel is available and some measurement of its variance along the time can be calculated. Pixel values can be represented by colours or tonalities in a two-dimensional graphic display.

All in all, the following distributions preferably can be displayed:
absolute impedance,
relative impedance,
lung perfusion and
phase-lag.

Furthermore, besides these basic modes of functional images, pixel values in the graphic display can also be determined by any mathematical and/or logical operation between the different basic modes. This leads e.g. to ventilation/perfusion, dispersion over time constants and/or image subtractions from the comparison of two modes.

As it can be noted the basic modes of functional images correspond to the four processing modes as described above. As a general rule, it can be assumed that the corresponding functional image of a processing mode is always displayed, if the corresponding processing mode leads to the determination of a bad lung condition. On the other hand, if a healthy lung condition is determined, it is advisable to further reduce the amount of data so that not the basic functional images, but appropriate graphs or numerical values are displayed.

Graphs

A graph is in principle a further data reduction with regard to a functional image and is preferably selected, if a healthy lung condition is determined. In principle, a graph is an online display of measured or calculated data representing selected regions of interest. Any form of graph can be chosen, like a line graph or a graphic bar.

Preferably, there are the following representations of graphs:
tidal ventilation of total lung,
tidal ventilation within a region of interest,
tidal ventilation within a plurality of lung regions,
ratio of ventilation within two regions of interest,
mean phase-lag of total lung,
mean phase-lag within a region of interest,
mean phase-lag within a plurality of lung regions,
ratio of ventilation within two regions of interest,
exponential curve for forced vital capacity manoeuvres as during lung function tests for the total lung and for any region of interest.

Numerical values

Numerical values are a further data reduction with regard to graphs or functional images. A numerical value in an online display of measured or calculated values representing condensed information on the entire lung or selected regions of interest. As it is applied for graphs, numerical values will be chosen as a selected screen mode, if a healthy lung condition is determined in accordance with the results of the predetermined processing modes.

Preferably, the following numerical values are assumed:
homogeneity index for ventilation within the total lung,
homogeneity index for ventilation within a region of interest,
ratio of ventilation in used impedance changes in selected parts of the lung, e.g. ventilation in used impedance changes of the upper lung divided by the lower lung,
homogeneity index for perfusion within the total lung,
homogeneity index for perfusion within a region of interest,
ratios of perfusion in selected parts of the lung like the upper/lower ratio,
homogeneity index for phase-lag within the total lung,
homogeneity index for phase-lag within a region of interest,
ratios of perfusion in selected parts of the lung like the upper/lower ratio,
numerical value or a time constant for characterizing a forced vital capacity manoeuvre as during lung function tests for the total lung and/or for any region of interest.

Others

Of course, any other suitable screen mode is possible for displaying the EIT data appropriately. One possibility is an adapted decision support display which can be selected and/or adapted in advance. One form of an adapted-decision support display can be a display for making clinical titration of the positive end-expiratory pressure (PEEP) easy. The display can consist of a coloured vertical or horizontal bar. The colours range symmetrically from green in the very centre via yellow and orange to dark red at both ends of the bar. Red indicates too high or too low levels of PEEP, whereas green indicates the optimal PEEP range, Any other combination of colours or shading of one single colour may be used, too. A marker within the bar indicates the current level of PEEP. Too high levels of PEEP will place the marker into the upper or the right red field, wherein too low levels of PEEP will move the marker downward or to the left. When operating the mechanical ventilator, the user will just watch the marker move within the bar. Once the marker has reached the middle of the green zone, PEEP should have reached its optimal level.

In accordance with one aspect of the invention, the screen mode is updated on demand of a user. This means that the display of the selected is frozen until the user requests another update of the underlying data of the display.

In accordance with another aspect of the invention, the displayed EIT data are updated in real time. This means that each display uses the data which are actually acquired from the patient's body. If necessary, a running time window can be used in order to achieve a further noise reduction.

In accordance with another aspect of the present invention, an estimate of a pathological condition is input by a user, wherein processing of the EIT data is carried out with a subcombination of the predetermined processing modes in accordance with the estimated pathological condition. In case when the doctor has already an idea of the pathological condition of the examined part of the patient's body, it can be taken advantage of this knowledge by providing a corresponding input format.

In accordance with another aspect of the present invention, said part of the patient's body to be examined is the patient's lung. Using the method of electrical impedance tomography, it has shown very advantageous to examine a patient's lung because very high impedance changes in the zone of the thorax are caused by breathing in and out of air so that the zone of the thorax shows good contrasts. Using as processing modes the above-described relative mode, phase-lag mode, perfusion mode and absolute mode, the following logic can be applied for determining specific lung conditions:

The lung condition of a pulmonary infarct is determined, if the relative mode yields a low result, the perfusion mode yields a low result and the absolute mode yields a low result.

The lung condition of a pulmonary embolism is determined, if the relative mode yields a normal result, the perfusion mode yields a low result and the absolute mode yields a normal result.

The lung condition of a localized pneumonia is determined, if the relative mode yields a low result, the perfusion yields a high result and the absolute mode yields a low result.

The lung condition of an emphysema-like area is determined, if the relative mode yields a low result, the perfusion yields a low result and the absolute mode yields a high result.

The lung condition of a cyclic airway closure is determined, if the relative mode yields a high result, the phase-lag mode yields a very high result and the absolute mode yields an unsteady result.

The lung condition of persistent airway closure with air-trapping is determined, if the relative mode yields a very low result, the phase-lag mode yields a very high result and the absolute mode yields an unsteady result.

The lung condition of a persistent airway closure with re-absorption atelaktasis is determined, if the relative mode yields a very low result, the phase-lag mode yields an unsteady result and the absolute mode yields a very low result.

The above-described logic to determine specific lung conditions can be based on the principles of Fuzzy Logic. Each term of "low" and "high" has to be described in certain numerical ranges with regard to the respective processing mode. This can be done, e.g., by examining a patient with a healthy lung and determining the numerical ranges for each processing mode which can be applied for healthy conditions. "Low" and "high" deviations from these reference values can also be expressed by certain ranges of values.

According to a further aspect of the present invention, a screen mode consists of graphic elements which are pre-stored in a data store as graphic patterns and which are fetched from the data store as soon as the corresponding screen mode is selected. Thereby a faster graphic display can be achieved because the graphic elements which involve time-consuming build-up of the display are pre-stored already, wherein only changes with regard to the actual EIT data have to be updated in the pre-stored display.

BRIEF DESCRIPTION OF THE DRAWINGS

The invention will now be described by way of an example and with reference to the accompanying drawings in which:

FIG. 1 shows the four principle conditions of alveoli,

FIG. 4a shows the determination of specific lung conditions in accordance with different processing modes, FIG. 4b shows the selection of screen modes in accordance with the specific lung conditions according to FIG. 4a, FIG. 5a shows the determination of specific lung conditions in accordance with different processing modes, FIG. 5b shows the selection of screen modes in accordance with the specific lung conditions according to FIG. 5a, FIG. 6a shows the determination of specific lung conditions in accordance with different processing nodes, FIG. 6b shows the selection of screen modes in accordance with the specific lung conditions according to FIG. 6a, FIG. 7a shows the determination of specific lung conditions in accordance with different processing modes, FIG. 7b shows the selection of screen modes in accordance with the specific lung conditions according to FIG. 7a, FIG. 8a shows the determination of specific lung conditions in accordance with different processing modes, FIG. 8b shows the selection of screen modes in accordance with the specific lung conditions according to FIG. 8a, FIG. 9 shows the combined display of different screen modes.

DETAILED DESCRIPTION OF THE INVENTION

Figure 2:
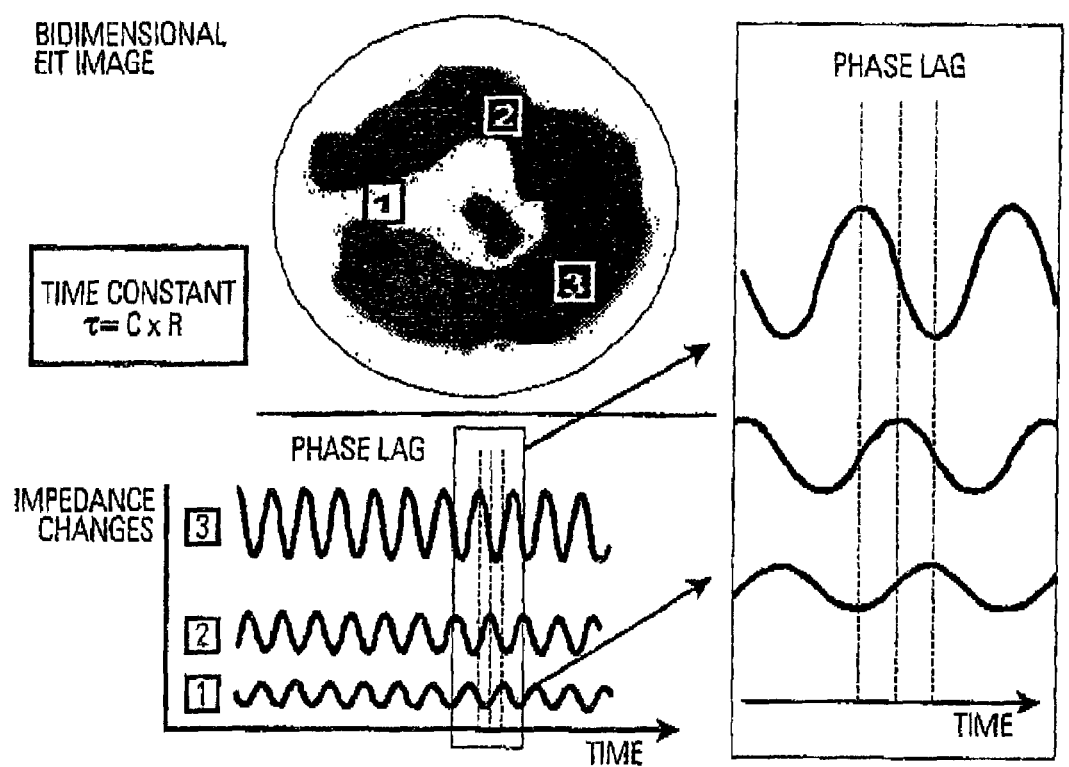
FIG. 2 shows the processing of EIT data according to the phase-lag mode.
Figure 3:
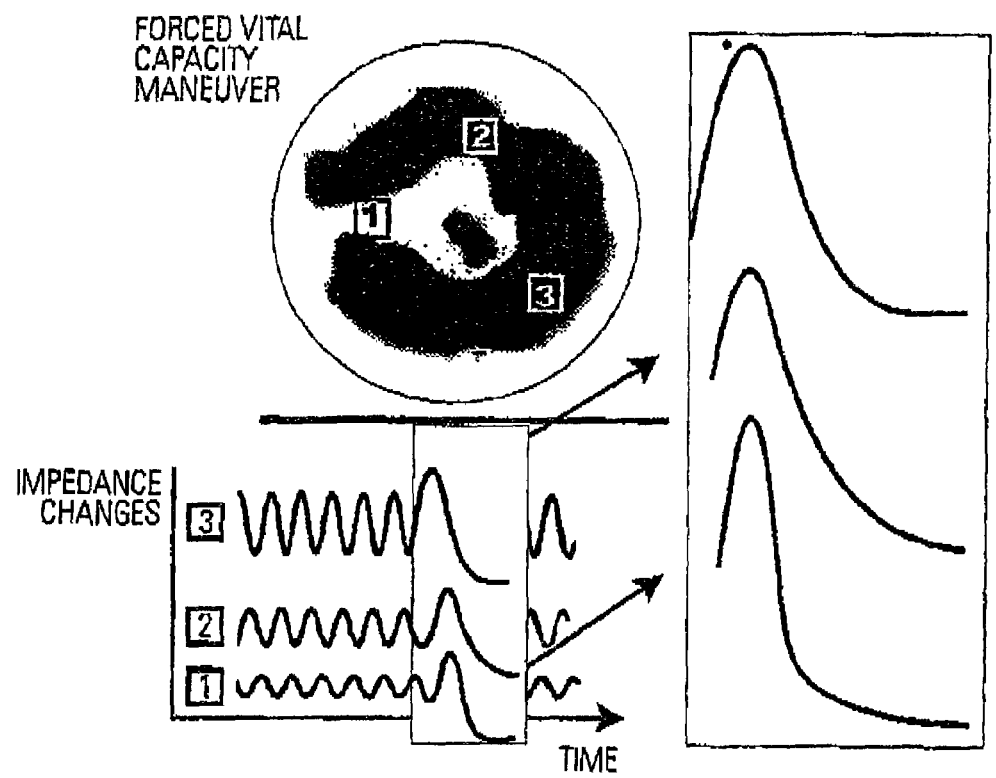
FIG. 3 shows the processing of EIT data according to the time constant mode.

As to the figures FIG. 1 to FIG. 3 it is referred to the description above.

FIGS. 4 to 8 show the determination of specific lung conditions in accordance with the results of predetermined processing modes and consequently the selection of screen modes in accordance with the determined specific lung conditions. For the determination of the specific lung conditions and the selection of the screen modes, a tabular representation is used. Within each table field an indicator shows the deviation from a normal result of a processing mode or a normal range of a screen mode. An up-turned error means a deviation to a value which is higher than the normal value, whereas a down-turned error means the deviation from the normal value by a lower value, Two or more errors indicate a strong deviation. Opposite errors indicate strong deviations around the normal value.

The lung conditions according to FIGS. 4 to 7 refer to pathological conditions which usually affect only specific areas of the patient's lung. Therefore, as a overall principle according to the FIGS. 4 to 7, the selected screen modes correspond to the processing modes, if the determined specific lung conditions are bad, i.e. not healthy. The reason for this is that in the case of a bad lung condition the doctor should have the same information available which led to the automatic determination of said lung condition in order to examine and approve the determined lung condition. However, if no bad lung condition is determined according to the FIGS. 4 to 7, it is generally suggested to display overall graphs or overall numerical values which lead to a further data reduction. Examples of suitable graphs and numerical values are already listed above.

Another case is the determination of lung conditions which affect usually not a specific area of the lung, but the lung in total. In this case, the lung conditions can be characterized more specifically by adding the following values to the display:

numerical value for the overall ventilation homogeneity,
numerical value for the overall phase-lag homogeneity,
numerical value for ratio of upper/lower lung ventilation— and used impedance variation and
numerical value for ratio of upper/lower lung phase-lag.

FIG. 4 shows the determination of specific lung conditions on the basis of three processing modes, namely the relative mode, the perfusion and the absolute mode. This enables the diagnosis of pulmonary infarct, pulmonary embolism, localized pneumonia and/or emphysema-like area. As soon an a specific lung condition is determined according to FIG. 4a, the functional images according to FIG. 4b will be provided in accordance with the determined specific lung conditions and in accordance with the specified ranges according to FIG. 4b.

Further optimisation of the determination of those specific lung conditions can be achieved by additionally using a relative/perfusion mode (V/Q) which is derived from the relative mode and the perfusion mode by calculating the pixel-by-pixel ratio of both modes for each pixel. In this way, one can achieve a better discrimination of the conditions according to FIG. 4a. The corresponding determination of the specific lung conditions is shown in FIG. 5a. Again, the selection of the screen modes according to FIG. 5b results in functional images which relate to the corresponding processing modes.

FIGS. 6 and 7 show another example of the selection of screen modes on the basis of another set of specific lung conditions. More particular, the specific lung conditions are pneumothorax, pleural effusion, atelektasis and over-distension.

The combination of three modes (relative, absolute and perfusion mode) enables the determination of pneumothorax or pleural effusion; both pathologies are represented by zones of low variance—so-called silent zones in the relative mode. While a pneumothorax is characterized by a circumscribed zone of high impedance values in the absolute mode, a pleural effusion is associated with low values. The image obtained in the absolute mode can be superimposed or compared to the images obtained in the other modes. An aerated area (high absolute values) extending outside the zones of high relative dispersions (great tidal oscillation of relative impedance) represents a collection of air possibly due to barotraumas (destruction of lung tissue by mechanical ventilation or the disease process). A condensed area, with liquid-like absolute impedance extending outside the zones of high tidal oscillation (in relative impedance) represents a collection of fluid, most likely a pleural effusion or a totally collapsed part of the lung.

Corresponding to the representation according to FIG. 5, FIG. 7 shows again the improvement of the processing with regard to the specific lung conditions by adding a relative/perfusion mode (V/Q), in which each pixel represents the pixel-by-pixel ratio between the pixel value in the relative mode and the corresponding pixel value in the perfusion mode. However, for the above lung conditions, the addition of the relative/perfusion mode does not add any display information since an area of pneumothorax and effusion shows neither ventilation nor perfusion. Furthermore, the relative/perfusion does not help in differentiating between atelaktasis and over-distension. Therefore, in FIG. 7b only the functional images according to the relative mode, the perfusion mode and the absolute mode are suggested.

Finally, FIG. 8a shows the combination of the relative mode, the phase-lag mode and the absolute mode for the determination of patent airway, cyclic airway closure, persistent airway closure with air trapping and persistent airway closure with re-absorption atelaktasis.

Even if the relative mode shows a homogeneous distribution of ventilation induced variance across the sectional plane of the thorax, a significant phase-lag means that some problems in the small airways may be present (small airway closure, for instance, due to emphysema, COPD, surfactant deficiency, or ARDS). The presence of patent airways all across the lung parenchyma can only be guaranteed when both modes (the relative and the phase-lag) present a homogenous lung inflation/deflation. Therefore, the coincidence of a phase-lag-delay within an area presenting a reasonable relative variance of impedance will be used as a sign of cyclic airway closure.

As to the selection of screen modes, it is suggested according to FIG. 8b to display only the functional image according to the relative mode and the phase-lag mode, but not the functional image according to the absolute mode.

Figure 9:
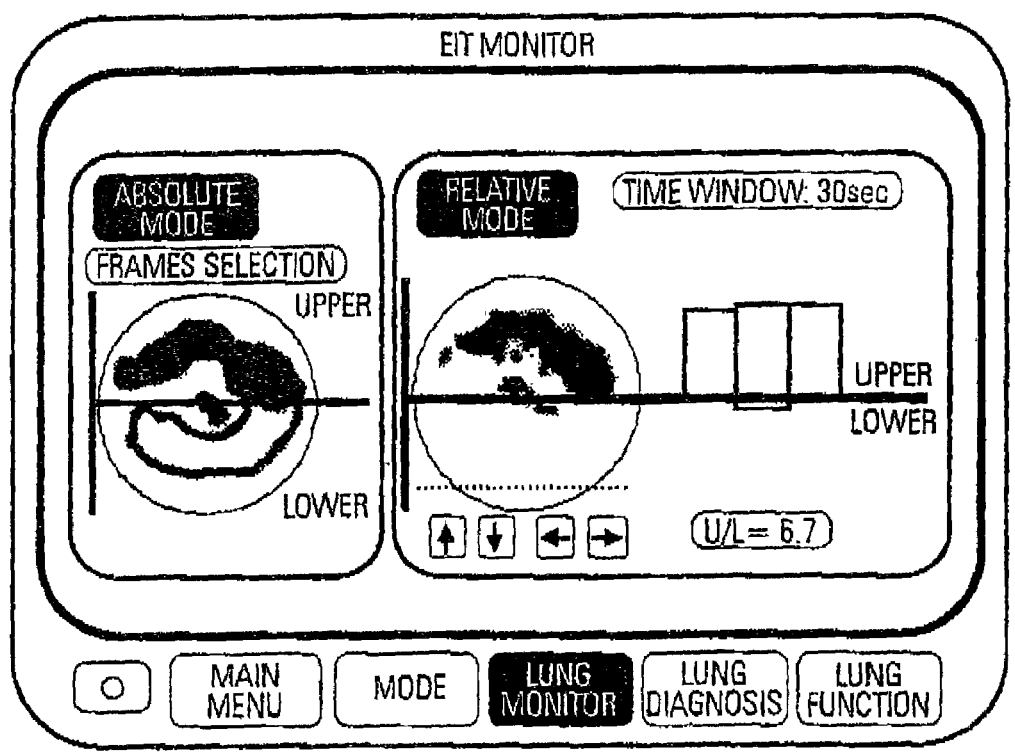

FIG. 9 shows an example of the selection of screen modes by displaying the combination of the absolute mode and the relative mode. Additionally, the same display may show different information on different parts of the screen at the same time like the following example:
  a functional image of dispersion (e.g. the standard deviation of ventilation and used impedance changes in each pixel),
  a numerical value representing a global functionality (e.g. overall homogeneity index of the total lung's ventilation),
  a graph representing calculated global or regional functionality (say ventilation and used impedance changes of the total lung),
  a numerical value representing calculated regional functionality (e.g. ventilation- and used impedance changes of the upper lung divided by the lower lung).

Figure 10:
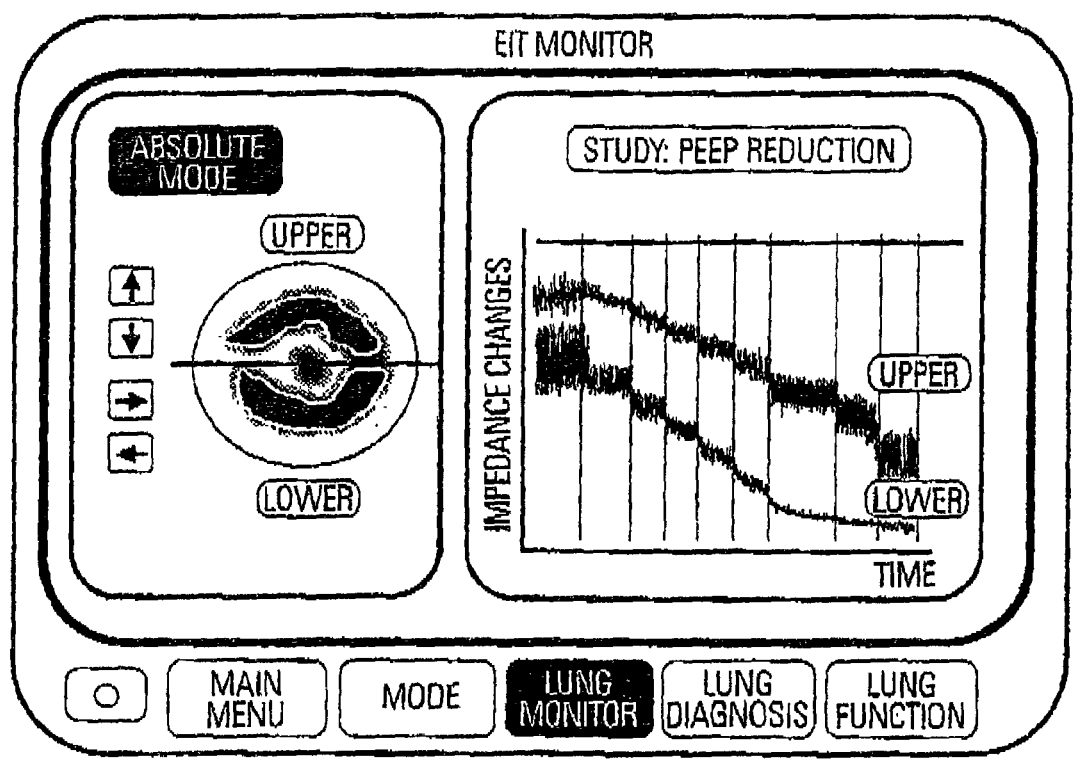
FIG. 10 shows the combined display of another combination of screen modes

FIG. 10 shows the combination of the functional image of the absolute mode and a decision support display. In this case, the decision support display is a graph of impedance changes over time of the upper lung and the lower lung when performing a PEEP-reduction (PEEP=Positive End-Expiratory Pressure).

Figure 11:
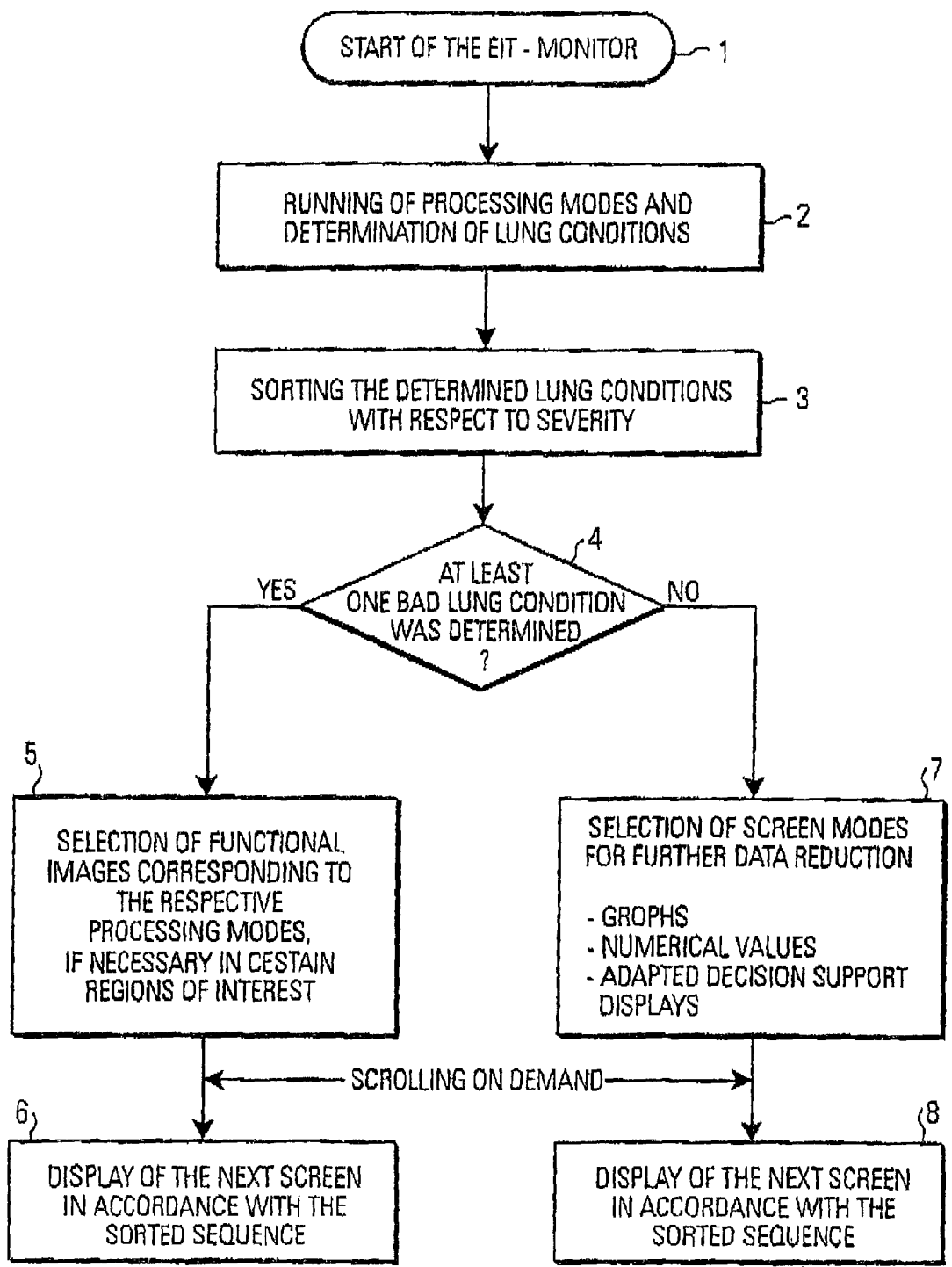
FIG. 11 shows a flow chart for performing the method according to the invention and FIG. 12 shows the integration of an apparatus according to the invention in a closed-loop ventilation system.

FIG. 11 shows a flow chart for performing the method according to the invention. In step 1, the EIT monitor is started, either by pressing a separate start button or by simply switching on the EIT monitor. In step 2, predetermined processing modes are run for determining specific lung conditions. As described above, suitable processing modes are the relative mode, the perfusion mode, the absolute mode and the phase-lag mode. The determination of specific lung conditions can be carried out as described according to the FIGS. 4a, 5a, 6a, 7a and 8a.

The result of step 2 is an evaluation of different lung conditions for different regions of interest of the lung. Hence, a plurality of determined lung conditions are available. It has to be further noted that the determination of the lung conditions usually leads to both lung conditions with severe problems and other lung conditions with a healthy condition, Therefore, in step 3, a sorting of all determined lung conditions with respect to their severity takes place, in order to display the corresponding screen modes in accordance with their importance. In step 4, a decision is taken whether at least one bad lung condition was determined. If yes, further processing takes place with step 5, otherwise processing is continued with step 7. The reason for the decision in step 4 is the fact that for a complete healthy lung it is advisable to perform a further data reduction when selecting screen modes, whereas in case of at least one bad lung condition a selection of screen modes should take place in accordance with the processing modes which led to the bad result.

Consequently, in step 5, a selection of screen modes takes place of functional images corresponding to the respective processing modes, if necessary in certain regions of interest. If necessary, then the user has got the possibility to scroll through various screen modes in accordance with the sorted sequence according to step 4.

On the other hand, if there are only healthy lung conditions determined, a selection of screen modes for further data reduction takes place in step 7. Suitable screen modes for further data reduction are e.g. graphs, numerical values or other adapted decision support displays. As already described according to step 6, there is again a possibility in step 8 to scroll on demand through the display to the next screen in accordance with the sorted sequence as sorted in step 4.

Figure 12:
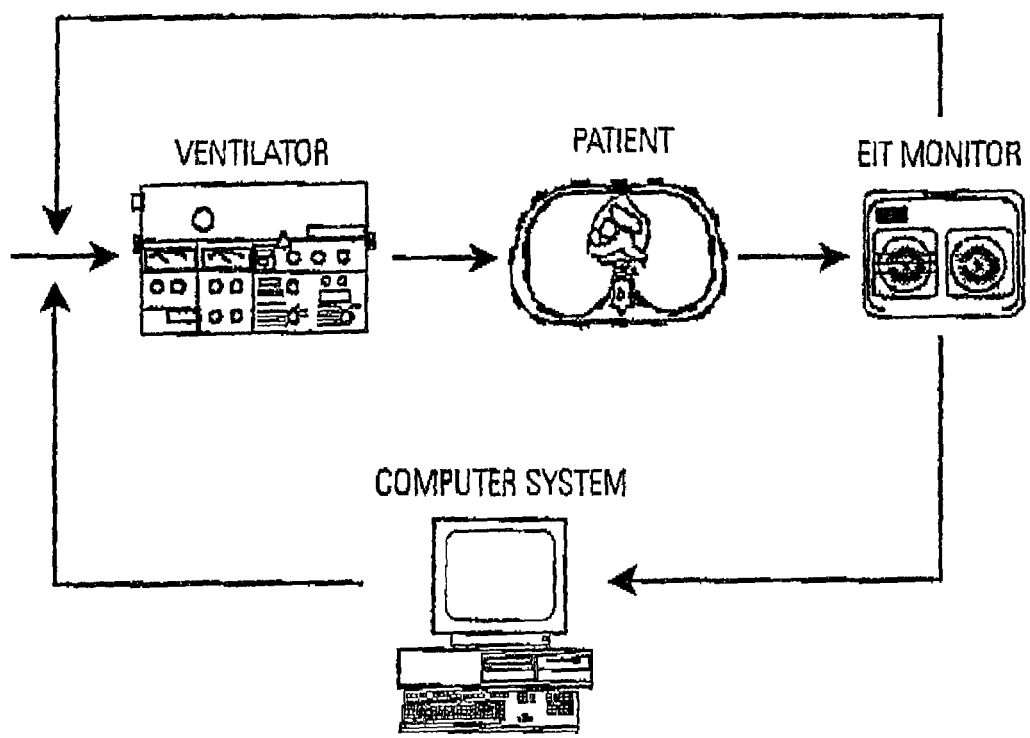

FIG. 12 shows the integration of an apparatus according to the invention in a closed-loop ventilation system. It has to be observed that the EIT monitor according to the invention yields already all necessary data which can be used by a ventilator for a closed-loop control. It might be also possible to provide an input format for the doctor for inputting limiting values with regard to the respiration pressure for closing and opening the lung.

The invention claimed is:

1. Method for displaying information obtained by electrical impedance tomography (EIT) data from a part of a patient's body on an EIT monitor, comprising the steps of:
implementing on said EIT monitor a plurality of predetermined processing modes and a plurality of predetermined screen modes,
providing the predetermined screen modes with functional images having an online imaging corresponding to one of the processing modes and with screen modes yielding further data reduction compared with the functional images,
processing the EIT data with said plurality of predetermined processing modes,
determining specific pathological conditions of said part in accordance with the results of the predetermined processing modes, selecting a functional image as a screen mode which corresponds to a respective processing mode, if said processing mode leads to the determination of a pathological condition, and selecting a screen mode which provides a further data reduction, if not a pathological condition is determined, and
displaying the EIT data in accordance with the selected screen modes.

2. Method according to claim 1, wherein the screen mode is updated on demand of a user.

3. Method according to claim 1, wherein the displayed EIT data are updated in real time.

4. Method according to claim 1, wherein the EIT data are calculated on the basis of a running data window.

5. Method according to claim 1, wherein an estimate of a pathological condition is input by a user and wherein processing of the EIT data is carried out with a subcombination of the predetermined processing modes in accordance with the estimated pathological condition.

6. Method according to claim 1, wherein a screen mode consists of graphic elements which are pre-stored in a data store as graphic patterns and which are fetched from the data store as soon as the corresponding screen mode is selected.

7. Method according to claim 1, wherein said part to be examined is a patient's lung or selected regions thereof.

8. Method according to claim 7, wherein a relative mode is implemented as a predetermined processing mode which yields as a result the mean variation of impedance changes due to ventilation.

9. Method according to claim 8, wherein a perfusion mode is implemented as a predetermined processing mode which yields as a result the mean variation of impedance changes due to lung perfusion, and
a perfusion ratio mode is implemented which calculates the ratio of the results of the relative mode and the perfusion mode and which yields as a result the ventilation/perfusion ratio.

10. Method according to claim 8, wherein a perfusion mode is implemented as a predetermined processing mode which yields as a result the mean variation of impedance changes due to lung perfusion,
an absolute mode is implemented as a predetermined processing mode which yields as a result the mean absolute impedance, and
the lung condition of a pulmonary infarct is determined, if the relative mode yields a low result, the perfusion mode yields a low result and the absolute mode yields a low result.

11. Method according to claim 8, wherein a perfusion mode is implemented as a predetermined processing mode which yields as a result the mean variation of impedance changes due to lung perfusion,
an absolute mode is implemented as a predetermined processing mode which yields as a result the mean absolute impedance, and
the lung condition of a pulmonary embolism is determined, if the relative mode yields a normal result, the perfusion mode yields a low result and the absolute mode yields a normal result.

12. Method according to claim 8, wherein a perfusion mode is implemented as a predetermined processing mode which yields as a result the mean variation of impedance changes due to lung perfusion,
an absolute mode is implemented as a predetermined processing mode which yields as a result the mean absolute impedance, and
the lung condition of a localized pneumonia is determined, if the relative mode yields a low result, the perfusion mode yields a high result and the absolute mode yields a low result.

13. Method according to claim 8, wherein a perfusion mode is implemented as a predetermined processing mode which yields as a result the mean variation of impedance changes due to lung perfusion,
an absolute mode is implemented as a predetermined processing mode which yields as a result the mean absolute impedance, and
the lung condition of an emphysema-like area is determined, if the relative mode yields a low result, the perfusion mode yields a low result and the absolute mode yields a high result.

14. Method according to claim 8, wherein a phase-lag mode is implemented as a predetermined processing mode which yields as a result the mean phase lag of impedance changes with regard to ventilation changes,
an absolute mode is implemented as a predetermined processing mode which yields as a result the mean absolute impedance, and
the lung condition of a cyclic airway closure is determined, if the relative mode yields a high result, the phase-lag mode yields a very high result and the absolute mode yields an unsteady result.

15. Method according to claim 8, wherein a phase-lag mode is implemented as a predetermined processing mode which yields as a result the mean phase lag of impedance changes with regard to ventilation changes,
an absolute mode is implemented as a predetermined processing mode which yields as a result the mean absolute impedance, and
the lung condition of a persistent airway closure with air-trapping is determined, if the relative mode yields a very low result, the phase-lag mode yields a very high result and the absolute mode yields an unsteady result.

16. Method according to claim 8, wherein a phase-lag mode is implemented as a predetermined processing mode which yields as a result the mean phase lag of impedance changes with regard to ventilation changes,
- an absolute mode is implemented as a predetermined processing mode which yields as a result the mean absolute impedance, and
- the lung condition of a persistent airway closure with re-absorption atelectasis is determined, if the relative mode yields a very low result, the phase-lag mode yields an unsteady result and the absolute mode a very low result.

17. Method according to claim 7, wherein a phase-lag mode is implemented as a predetermined processing mode which yields as a result the mean phase lag of impedance changes with regard to ventilation changes.

18. Method according to claim 7, wherein a perfusion mode is implemented as a predetermined processing mode which yields as a result the mean variation of impedance changes due to lung perfusion.

19. Method according to claim 7, wherein an absolute mode is implemented as a predetermined processing mode which yields as a result the mean absolute impedance.

20. Method according to claim 7, wherein each pixel of a functional image presents the estimate of its spatial location inside the lung and is displayed according to its distribution of conductivity according to the corresponding processing mode.

21. Method according to claim 7, wherein the screen modes providing further data reduction comprise numerical values of measured or calculated values representing condensed information on the entire lung or selected regions of interest.

22. Method according to claim 7, wherein the screen modes providing further data reduction comprise graphs of measured or calculated data representing condensed information on the entire lung or selected regions of interest.

23. Apparatus for displaying information obtained by electrical impedance tomography (EIT) data from a part of a patient's body on an EIT monitor,
- said EIT monitor comprising an implementation of a plurality of predetermined processing modes and of a plurality of predetermined screen modes, wherein the predetermined screen modes further comprise functional images with an online imaging corresponding to one of the processing modes and screen modes yielding further data reduction compared with the functional images,
- said apparatus further comprising:
- means for processing the EIT data with said plurality of predetermined processing modes,
- means for determining specific pathological conditions of said part in accordance with the results of the predetermined processing modes,
- means for selecting a functional image as a screen mode which corresponds to a respective processing mode, if said processing mode leads to the determination of a pathological condition, and means for selecting a screen mode which provides a further data reduction, if not a pathological is determined, and
- means for displaying the EIT data in accordance With the selected screen modes.

24. Apparatus according to claim 23, wherein the screen mode is updated on demand of a user.

25. Apparatus according to claim 23, wherein the displayed EIT data are updated in real time.

26. Apparatus according to claim 23, wherein the EIT data are calculated on the basis of a running data window.

27. Apparatus according to claim 23, wherein an estimate of a pathological condition is input by a user and wherein processing of the EIT data is carried out with a subcombination of the predetermined processing modes in accordance with the estimated pathological condition.

28. Apparatus according to claim 23, wherein a screen mode consists of graphic elements which are pre-stored in a data store as graphic patterns and which fetched from the data store as soon as the corresponding screen mode is selected.

29. Method according to claim 23, wherein said part to be examined is a patient's lung or selected regions thereof.

30. Apparatus according to claim 29, wherein a relative mode is implemented as a predetermined processing mode which yields as a result the mean variation of impedance changes due to ventilation.

31. Apparatus according to claim 30, wherein a perfusion mode is implemented as a predetermined processing mode which yields as a result the mean variation of impedance changes due to lung perfusion, and
- a perfusion ratio mode is implemented which calculates the ratio of the results of the relative mode and the perfusion mode and which yields as a result the ventilation/perfusion ratio.

32. Apparatus according to claim 30, wherein a perfusion mode is implemented as a predetermined processing mode which yields as a result the mean variation of impedance changes due to lung perfusion,
- an absolute mode is implemented as a predetermined processing mode which yields as a result the mean absolute impedance, and
- the lung condition of a pulmonary infarct is determined, if the relative mode yields a low result, the perfusion mode yields a low result and the absolute mode yields a low result.

33. Apparatus according to claim 30, wherein a perfusion mode is implemented as a predetermined processing mode which yields as a result the mean variation of impedance changes due to lung perfusion,
- an absolute mode is implemented as a predetermined processing mode which yields as a result the mean absolute impedance, and
- the lung condition of a pulmonary embolism, is determined, if the relative mode yields a normal result, the perfusion mode yields a low result and the absolute mode yields a normal result.

34. Apparatus according to claim 30, wherein a perfusion mode is implemented as a predetermined processing mode which yields as a result the mean variation of impedance changes due to lung perfusion,
- an absolute mode is implemented as a predetermined processing mode which yields as a result the mean absolute impedance, and
- the lung condition of a localized pneumonia is determined, if the relative mode yields a low result, the perfusion mode yields a high result and the absolute mode yields a low result.

35. Apparatus according to claim 30, wherein a perfusion mode is implemented as a predetermined processing mode which yields as a result the mean variation of impedance changes due to lung perfusion,
- an absolute mode is implemented as a predetermined processing mode which yields as a result the mean absolute impedance, and
- the lung condition of an emphysema-like area is determined, if the relative mode yields a low result, the perfusion mode yields a low result and the absolute mode yields a high result.

36. Apparatus according to claim 30, wherein a phase-lag mode is implemented as a predetermined processing mode which yields as a result the mean phase lag of impedance changes with regard to ventilation changes, an absolute mode is implemented as a predetermined processing mode which yields as a result the mean absolute impedance, and the lung condition of a cyclic airway closure is determined, if the relative mode yields a high result, the phase-lag mode yields a very high result and the absolute mode yields an unsteady result.

37. Apparatus according to claim 30, wherein a phase-lag mode is implemented as a predetermined processing mode which yields as a result the mean phase lag of impedance changes with regard to ventilation changes, an absolute mode is implemented as a predetermined processing mode which yields as a result the mean absolute impedance, and the lung condition of a persistent airway closure with air-trapping is determined, if the relative mode yields a very low result, the phase-lag mode yields a very high result and the absolute mode yields an unsteady result.

38. Apparatus according to claim 30, wherein a phase-lag mode is implemented as a predetermined processing mode which yields as a result the mean phase lag of impedance changes with regard to ventilation changes, an absolute mode is implemented as a predetermined processing mode which yields as a result the mean absolute impedance, and the lung condition of a persistent airway closure with re-absorption atelectasis is determined, if the relative mode yields a very low result, the phase-lag mode yields an unsteady result and the absolute mode a very low result.

39. Apparatus according to claim 29, wherein a phase-lag mode is implemented as a predetermined processing mode which yields as a result the mean phase lag of impedance changes with regard to ventilation changes.

40. Apparatus according to claim 29, wherein a perfusion mode is implemented as a predetermined processing mode which yields as a result the mean variation of impedance changes due to lung perfusion.

41. Apparatus according to claim 29, wherein an absolute mode is implemented as a predetermined processing mode which yields as a result the mean absolute impedance.

42. Apparatus according to claim 29, wherein each pixel of a functional image presents the estimate of its spatial location inside the lung and is displayed according to its distribution of conductivity according to the corresponding processing mode.

43. Apparatus according to claim 29, wherein the screen modes providing further data reduction comprise numerical values of measured or calculated values representing condensed information on the entire lung or selected regions of interest.

44. Apparatus according to claim 29, wherein the screen modes providing further data reduction comprise graphs of measured or calculated data representing condensed information on the entire lung or selected regions of interest.

\* \* \* \* \*